(12) United States Patent
Putman et al.

(10) Patent No.: US 7,888,394 B2
(45) Date of Patent: Feb. 15, 2011

(54) SYNTHESIS, POLYMORPHS, AND PHARMACEUTICAL FORMULATION OF FAAH INHIBITORS

(75) Inventors: David Putman, Irvine, CA (US); Olivier Dasse, Foothill Ranch, CA (US)

(73) Assignee: N.V. Organon, Oss (NL)

( * ) Notice: Subject to any disclaimer, the term of this patent is extended or adjusted under 35 U.S.C. 154(b) by 431 days.

(21) Appl. No.: 11/839,746

(22) Filed: Aug. 16, 2007

(65) Prior Publication Data

US 2009/0030074 A1 Jan. 29, 2009

Related U.S. Application Data

(60) Provisional application No. 60/823,076, filed on Aug. 21, 2006.

(51) Int. Cl.
*A61K 31/135* (2006.01)
*C07C 209/00* (2006.01)

(52) U.S. Cl. .................. 514/646; 564/305; 564/437

(58) Field of Classification Search ................ 564/305, 564/437; 514/646
See application file for complete search history.

(56) References Cited

U.S. PATENT DOCUMENTS

| 7,176,201 | B2 | 2/2007 | Piomelli et al. |
| 2007/0155707 | A1 | 7/2007 | Dasse et al. |
| 2007/0155747 | A1 | 7/2007 | Dasse et al. |
| 2008/0045513 | A1 | 2/2008 | Dasse et al. |
| 2008/0119549 | A1 | 5/2008 | Dasse et al. |

FOREIGN PATENT DOCUMENTS

WO WO 2004/033422 4/2004

WO WO 2004/033422 A2 4/2004

OTHER PUBLICATIONS

Kathuria et al., "Modulation of anxiety through blockade of anandamide hydrolysis," *Nat. Med.* 9 (2003) 76-81.
McKinney et al., "Structure and Function of Fatty Acid Amide Hydrolase," *Annu. Rev. Biochem.* 74 (2005) 411-432.
Mor et al., "Cyclohexylcarbamic Acid 3'- or 4'-Substituted Biphenyl-3-yl Esters as Fatty Acid Amide Hydrolase Inhibitors: Synthesis, Quantitative Structure-Activity Relationships, and Molecular Modeling Studies," *J. Med. Chem.* 47 (2004) 4998-5008.
Fegley, et al., "Characterization of the Fatty Acid Amide Hydrolase Inhibitor Cyclohexyl Carbamic Acid 3'-Carbamoyl-biphenyl-3-yl Ester (URB597): Effects on Anandamide and Oleoylethanolamide Deactivation", *The Journal of Pharmacology and Experimental Therapeutics* (2005) 313:1, 352-358.
Kathuria, et al., "Modulation of anxiety through blockade of anandamide hydrolysis", *Nature Medicine* (2003) 9:1, 76-81.
Mor, et al., "Cyclohexylcarbamic Acid 3'- or 4'-Substituted Biphenyl-3-yl Esters as Fatty Acid Amide Hydrolase Inhibitors: Synthesis, Quantitative Structure-Activity Relationships, and Molecular Modeling Studies", *Journal of Medicinal Chemistry* (2004) vol. 47, 4998-5008.
International Search Report issued on Nov. 21, 2007 in connection with PCT Intl. Appln. No. PCT/EP2007/058589.
U.S. Appl. No. 11/773,675, filed Jul. 5, 2007, Olivier Dasse, et al.
U.S. Appl. No. 11/772,597, filed Jul. 2, 2007, Olivier Dasse, et al.
U.S. Appl. No. 11/561,774, filed Nov. 6, 2006, Olivier Dasse, et al.
U.S. Appl. No. 11/617,147, filed Dec. 28, 2006, Olivier Dasse, et al.

*Primary Examiner*—Golam M Shameem
(74) *Attorney, Agent, or Firm*—Maria V. Marucci; Valerie J. Camara (57) ABSTRACT

Pharmacological inhibition of fatty acid amide hydrolase (FAAH) activity leads to increased levels of fatty acid amides. The alkylcarbamic acid aryl ester of Formula (I), KDS-4103, is a FAAH inhibitor. Described herein is a process for the preparation of the compound of Formula (I), characterization of polymorphs of the FAAH inhibitor, and their uses therof.

17 Claims, 5 Drawing Sheets

SYNTHESIS, POLYMORPHS, AND PHARMACEUTICAL FORMULATION OF FAAH INHIBITORS

FIELD OF THE INVENTION

Described herein is a process for the synthesis and pharmaceutical formulation of polymorphs of the FAAH inhibitor KDS-4103.

BACKGROUND OF THE INVENTION

Fatty acid amide hydrolase (FAAH) is an enzyme that hydrolyzes the fatty acid amide (FAA) family of endogenous signaling lipids. General classes of FAAs include the N-acylethanolamines (NAEs) and fatty acid primary amides (FAPAs). Examples of NAEs include anandamide (AEA), palmitoylethanolamide (PEA) and oleoylethanolamide (OEA). Pharmacological inhibition of FAAH activity results in increases in the levels of these fatty acid amides.

SUMMARY OF THE INVENTION

Processes for the preparation of a compound that inhibits the activity of fatty acid amide hydrolase, compositions that include the compound, as well as methods of use thereof are provided. In one embodiment, provided herein is a process for preparing of the alkylcarbamic acid aryl ester of Formula (I):

Formula (I)

KDS-4103 comprising the steps of:
(a) reacting cyclohexyl isocyanate with 3'-hydroxybiphenyl-3-carboxamide in the presence of an amine base in a suitable non-aromatic solvent; and isolating the alkylcarbamic acid aryl ester KDS-4103.

The process for preparing alkylcarbamic acid aryl esters of Formula (I), KDS-4103, includes a suitable non-aromatic solvent. In some embodiments the suitable non-aromatic solvent is selected from among acetonitrile and ethanol. In certain embodiments, the suitable non-aromatic solvent is acetonitrile.

The process for preparing alkylcarbamic acid aryl esters of Formula (I), KDS-4103, includes an amine base. In some embodiments, the amine base is a tertiary amine base. In other embodiments, the amine base is selected from among triethylamine, diisopropylethylamine, 1,2,2,6,6-pentamethylpiperidine, and tributylamine. In some other embodiments, the tertiary amine base is triethylamine.

In certain embodiments, the process for preparing alkylcarbamic acid aryl esters of Formula (I) includes isolating the alkylcarbamic acid aryl ester of Formula (I) (step (b)). In some embodiments, isolating the alkylcarbamic acid aryl ester of Formula (I) includes filtration.

In some embodiments, the process of preparing arylcarbamic acid aryl esters of Formula (I) includes preparing 3'-hydroxybiphenyl-3-carboxamide by a process that includes:
treating 3-hydroxyphenylboronic acid with 3-bromobenzamide in the presence of a heterogeneous palladium catalyst, an inorganic base, a phase-transfer catalyst, and a suitable organic solvent.

In certain embodiments, the heterogeneous palladium catalyst is selected from among $PdCl_2$, $Pd(OAc)_2$, and $Pd(OH)_2$. In other embodiments, the heterogeneous palladium catalyst is $PdCl_2$. In certain embodiments, the inorganic base is selected from among $Li_2CO_3$, $Na_2CO_3$, $K_2CO_3$, $Cs_2CO_3$, and NaOH. In some embodiments, the inorganic base is $K_2CO_3$. In some embodiments, the phase transfer catalyst is a tetra-alkyl ammonium halide. In some other embodiments, the phase transfer catalyst is $nBu_4NBr$.

In some embodiments, the process for preparing 3'-hydroxybiphenyl-3-carboxamide includes a suitable organic solvent selected from among methanol, ethanol, benzene, toluene, 1,4-dioxane, tetrahydrofuran, and water. In some other embodiments, the process for preparing 3'-hydroxybiphenyl-3-carboxamide includes ethanol.

In one embodiment, provided herein is a crystalline form of the compound KDS-4103

Figure 1:
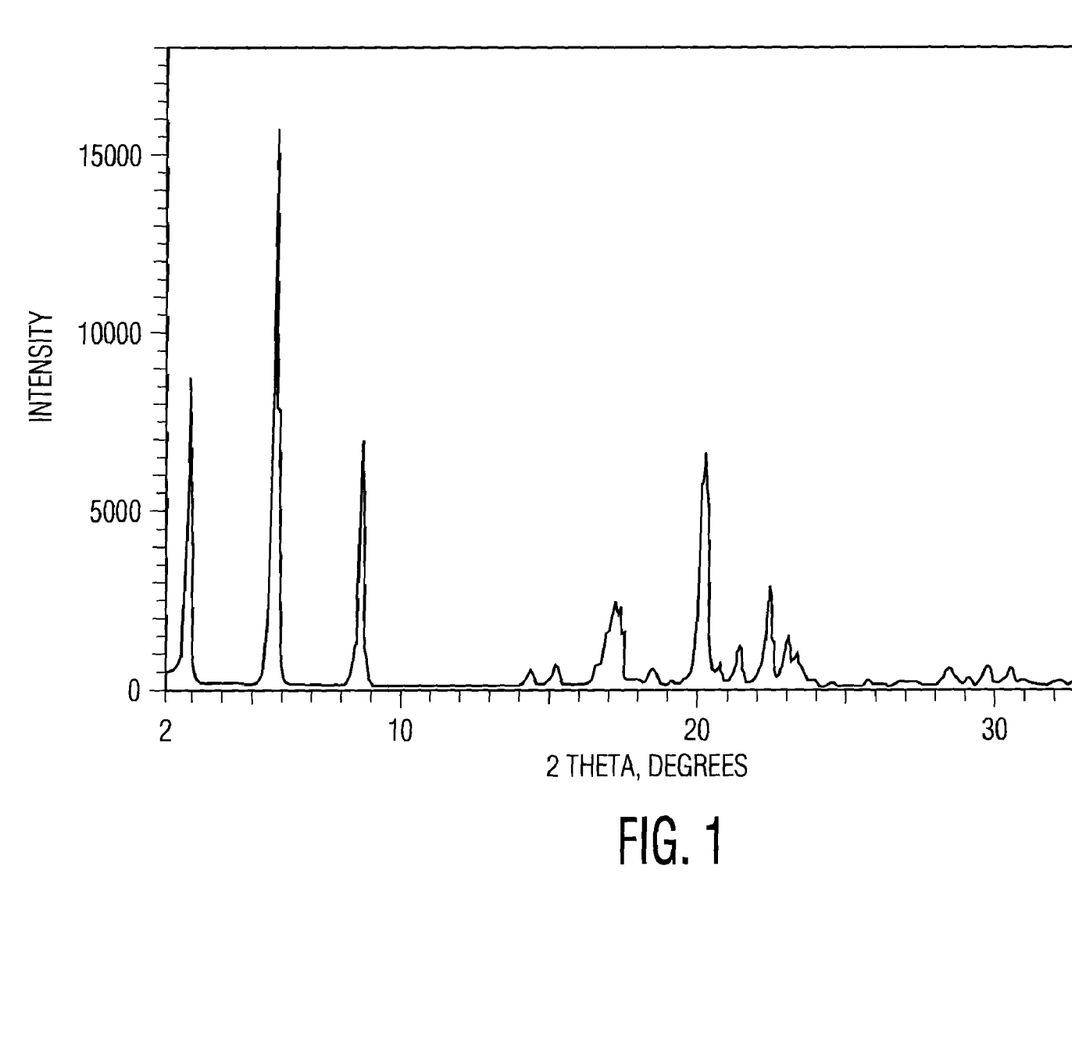
FIG. 1 is the X-ray powder diffraction pattern of the crystalline form of KDS-4103 crystallized from ethanol.
Figure 2:
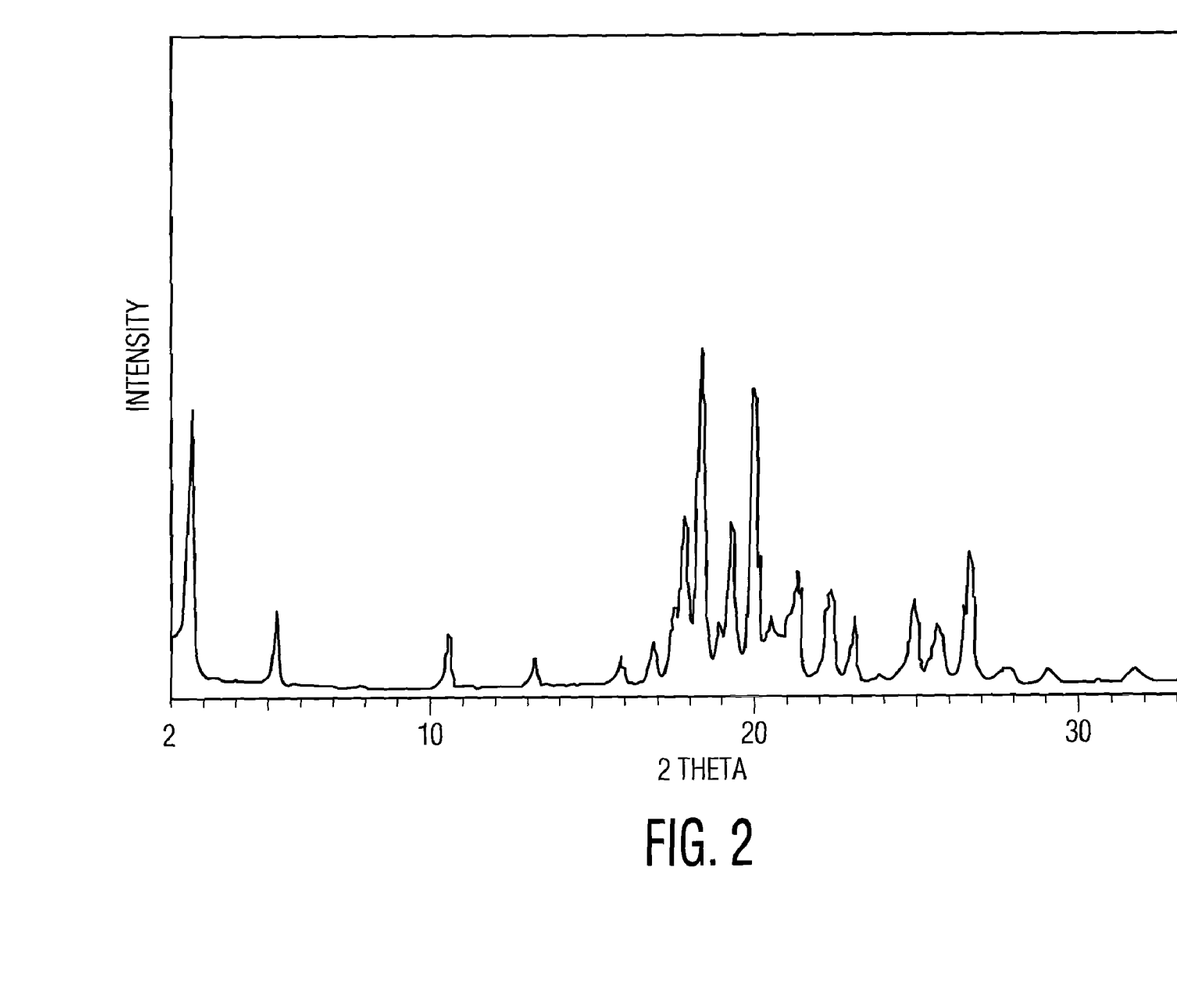
FIG. 2 is the X-ray powder diffraction pattern of the crystalline form of KDS-4103 crystallized from acetonitrile.

KDS-4103 which is characterized by a solid state X-ray powder diffraction XRPD pattern as shown in FIG. 1. In another embodiment, provided herein is a crystalline form of the compound KDS-4103, which is characterized by a solid state X-ray powder diffraction XRPD pattern as shown in FIG. 2.

Pharmaceutical compositions that include the compound KDS-4103, which is characterized by a solid state X-ray powder diffraction XRPD pattern as shown in FIG. 1, formulated for oral administration are also provided. In other embodiments, provided herein are pharmaceutical compositions that include the compound KDS-4103, which is characterized by a solid state X-ray powder diffraction XRPD pattern as shown in FIG. 2., formulated for oral administration.

In certain embodiments, the pharmaceutical compositions that include compound KDS-4103, which is characterized by a solid state X-ray powder diffraction XRPD pattern as shown in FIG. 1, are formulated into a dosage form selected from the group consisting of an aqueous oral dosage form, a solid oral dosage form, a controlled release formulation, a fast melt formulation, an effervescent formulation, a lyophilized formulation, a tablet, a capsule, a delayed release formulation, an extended release formulation, a pulsatile release formulation, a multiparticulate formulation, and mixed immediate release and controlled release formulations. In other embodiments, the pharmaceutical compositions that include compound KDS-4103, which is characterized by a solid state X-ray powder diffraction XRPD pattern as shown in FIG. 2, are formulated into a dosage form selected from the group consisting of an aqueous oral dosage form, a solid oral dosage form, a controlled release formulation, a fast melt formulation, an effervescent formulation, a lyophilized formulation, a tablet, a capsule, a delayed release formulation, an extended release formulation, a pulsatile release formulation, a multiparticulate formulation, and mixed immediate release and controlled release formulations.

In one embodiment, provided herein are methods for improving the bioavailability of KDS-4103 in a mammal that includes administering to the mammal the crystalline form of KDS-4103, which is characterized by a solid state X-ray powder diffraction XRPD pattern as shown in FIG. 1. In another embodiment, provided herein are methods for improving the bioavailability of KDS-4103 in a mammal that includes administering to the mammal the crystalline form of KDS-4103, which is characterized by a solid state X-ray powder diffraction XRPD pattern as shown in FIG. 2.

Also provided herein is the use of the crystalline form of KDS-4103, which is characterized by a solid state X-ray powder diffraction XRPD pattern as shown in FIG. 1, for the formulation of a medicament for oral delivery for the inhibition of fatty acid amide hydrolase (FAAH). In some embodiments, provided herein is the use of the crystalline form of KDS-4103, which is characterized by a solid state X-ray powder diffraction XRPD pattern as shown in FIG. 2., for the formulation of a medicament for oral delivery for the inhibition of fatty acid amide hydrolase (FAAH).

Articles of manufacture that include the crystalline form of KDS-4103, which is characterized by a solid state X-ray powder diffraction XRPD pattern as shown in FIG. 1, are also disclosed. In one embodiment, provided herein is an article of manufacture, including packaging material, the crystalline form of KDS-4103, which is characterized by a solid state X-ray powder diffraction XRPD pattern as shown in FIG. 1, which is effective for inhibiting the activity of fatty acid amide hydrolase (FAAH), within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for inhibiting the activity of fatty acid amide hydrolase (FAAH).

In other embodiments, articles of manufacture are provided that include the crystalline form of KDS-4103, which is characterized by a solid state X-ray powder diffraction XRPD pattern as shown in FIG. 2. In another embodiment, provided herein is an article of manufacture, including packaging material, the crystalline form of KDS-4103, which is characterized by a solid state X-ray powder diffraction XRPD pattern as shown in FIG. 2., which is effective for inhibiting the activity of fatty acid amide hydrolase (FAAH), within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for inhibiting the activity of fatty acid amide hydrolase (FAAH)

In another embodiment, provided herein is a crystalline form of the compound KDS-4103

KDS-4103 prepared by the process described herein, characterized by a solid state X-ray powder diffraction XRPD pattern as shown in FIG. 1. In other embodiments, provided herein is a crystalline form of the compound KDS-4103 prepared by the process described herein, characterized by a solid state X-ray powder diffraction XRPD pattern as shown in FIG. 2.

In certain embodiments, provided herein is a polymorph of KDS-4103, characterized by the XRPD pattern as shown in FIG. 1, which has a effective particle size distribution ranging from about 5 μm to about 36 μm, with an effective particle size of about 14 μm. In other embodiments, provided herein is a polymorph of KDS-4103, characterized by the XRPD pattern as shown in FIG. 2, which has a effective particle size distribution ranging from about 2 μm to about 12 μm, with an effective particle size of about 6 μm.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. All references cited herein, including patents, patent applications, and publications, are hereby incorporated by reference in their entirety.

BRIEF DESCRIPTION OF THE DRAWINGS

The novel features are set forth with particularity in the appended claims. A better understanding of the features and advantages of the present disclosure will be obtained by reference to the following detailed description that sets forth illustrative embodiments, in which the principles described herein are utilized, and the accompanying drawings of which:

DETAILED DESCRIPTION OF THE INVENTION

Fatty acid amide hydrolase (FAAH) is an enzyme that hydrolyzes the fatty acid amide (FAA) family of endogenous signaling lipids. General classes of FAAs include the N-acylethanolamines (NAEs) and fatty acid primary amides (FAPAs). Examples of NAEs include anandamide (AEA), palmitoylethanolamide (PEA) and oleoylethanolamide (OEA). An example of FAPAs includes 9-Z-octadecenamide or oleamide. (McKinney M K, Cravatt B F. 2005. *Annu Rev Biochem* 74:411-32)].

Diseases, disorders, syndromes and/or conditions, that would benefit from inhibition of FAAH enzymatic activity include, for example, Alzheimer's Disease, schizophrenia, depression, alcoholism, addiction, suicide, Parkinson's disease, Huntington's disease, stroke, emesis, miscarriage, embryo implantation, endotoxic shock, liver cirrhosis, atherosclerosis, cancer, traumatic head injury, glaucoma, and bone cement implantation syndrome. Other diseases, disorders, syndromes and/or conditions that would benefit from inhibition of FAAH activity, include, for example, multiple sclerosis, retinitis, amyotrophic lateral sclerosis, immunodeficiency virus-induced encephalitis, attention-deficit hyperactivity disorder, pain, nociceptive pain, neuropathic pain, inflammatory pain, non-inflammatory pain, painful hemorrhagic cystitis, obesity, hyperlipidemia, metabolic disorders, feeding and fasting, alteration of appetite, stress, memory, aging, hypertension, septic shock, cardiogenic shock, intestinal inflammation and motility, irritable bowel syndrome, colitis, diarrhea, ileitis, ischemia, cerebral ischemia, hepatic ischemia, myocardial infarction, cerebral excitotoxicity, seizures, febrile seizures, neurotoxicity, neuropathies, sleep, induction of sleep, prolongation of sleep, insomnia, and inflammatory diseases.

Carbamic acid esters have shown promise as selective FAAH inhibitors (Kathuria et al., *Nat. Med.* 2003, 9:76-81). In particular, a series of alkylcarbamic acid aryl esters, such as, for example, the compound of Formula (I) disclosed herein, have been shown to be potent and selective inhibitors of FAAH activity. Mor et al. (*J. Med. Chem.* 2004, 47:4998-5008; incorporated by reference) and Piomelli et al. (International Patent Publication No. WO 2004/033422; incorporated by reference) disclosed representative alkylcarbamic acid aryl esters of Formula (I) that are potent inhibitors of FAAH activity, but do not significantly interact with selected serine hydrolases or with cannabinoid receptors. Among the disclosed alkylcarbamic acid esters of Formula (I), the compound cyclohexylcarbamic acid 3'-carbamoylbiphenyl-3-yl ester (also known as 5'-carbamoylbiphenyl-3-yl cyclohexyl carbamate, UCM597 and URB597; referenced herein as compound KDS-4103) was identified as a potent and selective inhibitor of FAAH activity.

KDS-4103 has the following structure:

KDS-4103 has a molecular weight of 338.4 and is a white crystalline solid at room temperature.

Mor et al. and Piomelli et al. disclose a process for the preparation of alkylcarbamic acid aryl esters of Formula (I), such as, for example, KDS-4103, that utilizes toxic solvents, such as, for example, toluene; utilizes air sensitive reagents, such as, for example homogeneous phosphine containing palladium catalysts; requires extensive purification protocols, such as, for example, column chromatography and recrystallization; and provides low yields (~30%) of the desired alkylcarbamic acid aryl ester product. Due to the use of homogeneous palladium catalysts that are utilized in the process disclosed by Mor et al. and Piomelli et al., contamination of the final active therapeutic compound with palladium species and/or phosphine species is a concern. The process described by Mor et al. and Piomelli et al. is not applicable on an industrial scale due to the potential for product contamination, the use of toxic solvents, the requirement for column chromatography, the low efficiency of the reactions, and the low overall yields of the synthetic process.

Therapeutic agents that are administrable to mammals, such as humans, must be prepared by following strict regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

The process disclosed by Mor et al. and Piomelli et al. utilizes toluene in the final step of the preparation of alkylcarbamic acid aryl esters, a class 2 solvent that is not desirable in the final step of a synthetic process for the preparation of a pharmaceutical for human use. As well, the process described by Mor et al. and Piomelli et al. provides the alkylcarbamic acid aryl esters, in low yields. For example, KDS-4103 was prepared in approximately 30% yield by the process disclosed by Mor et al. and Piomelli et al. Toluene was used as the solvent, and column chromatography was required in order to obtain the compound KDS-4103 in high purity.

Due to the therapeutic importance of alkyl carbamic acid aryl esters of Formula (I), such as, for example KDS-4103, a need exists for a synthetic process that avoids contamination of the final product with toxic solvents, by-products and/or reagents, and increases the efficiency of the overall process, thus making it amenable for the preparation of a therapeutic agent and/or composition on an industrial scale.

Described herein is a process for the preparation of KDS-4103 of Formula (I) that avoids the use of toxic solvents and minimizes the contamination of the final product(s) with toxic solvents, by-products and/or reagents. Described herein is a process for the preparation of KDS-4103 of Formula (I) in high yields, which avoids the need for time consuming and expensive purification methods, such as column chromatography. Described herein is a process for the preparation of KDS-4103 in high yield, which avoids toxic solvents, does not require oxygen-free reaction conditions, minimizes or eliminates by-product formation and/or contamination, and increases the efficiency of the overall synthetic process utilized to prepare this class of therapeutic compounds. Processes described herein for the preparation of KDS-4103, do not require column chromatography and provide a crystalline form of the compound that increases the oral bioavailability of the compound compared to previous synthetic protocols. The process disclosed herein has ease of operation, is cost effective, does not require purification of reaction products by re-crystallization or column chromatography and improves yields of final product.

Described herein is a process for the preparation of the alkylcarbamic acid aryl ester of Formula (I), KDS-4103, on an industrial scale (such as multi-kilogram scale). Described herein is a process for the preparation of KDS-4103 polymorphs on an industrial scale. Described herein is a process for the preparation of KDS-4103 polymorphs in high yield that have improved oral bioavailability. Described herein is a process for the preparation of KDS-4103 with a narrow effective particle size distribution. In one embodiment, the process disclosed herein includes the preparation of KDS-4103 with an improved effective particle size distribution. Described herein is a process for improving the effective average particle size distribution of KDS-4103. Described herein is a process for increasing the oral bioavailability of the compound of Formula (I), KDS-4103. Compositions that include polymorphs of KDS-4103, as disclosed herein, are also provided. Compositions that include that compound of Formula (I), KDS-4103, prepared by the process disclosed herein, are also provided. Polymorphs of the compound KDS-4103 that have increased oral bioavailability, are also provided.

The disclosed process enables improved yields of the carbamate derivative KDS-4103, and eliminates the need to purify reaction products. This process enables the preparation of the cycloalkyl carbamate derivative of Formula (I), KDS-4103, with increased yields, under mild reaction conditions, at less cost, and with fewer byproducts. The process disclosed herein is particularly applicable to large scale chemical production of therapeutic pharmacological products.

Described herein is a process for the preparation of the alkylcarbamic acid aryl ester of Formula (I)

Formula (I)

[structure of KDS-4103]

KDS-4103 including the steps of:
(a) reacting cyclohexyl isocyanate with 3'-hydroxybiphenyl-3-carboxamide in the presence of an amine base in a suitable non-aromatic solvent; and
(b) isolating the alkylcarbamic acid aryl ester of Formula (I).

The process for preparing the alkylcarbamic acid aryl ester of Formula (I), KDS-4103, includes a suitable non-aromatic solvent. In some embodiments, the suitable non-aromatic solvent is selected from among acetonitrile and ethanol. In some other embodiments, the suitable non-aromatic solvent is ethanol. In certain embodiments, the suitable non-aromatic solvent is acetonitrile.

The process for preparing the alkylcarbamic acid aryl ester of Formula (I), for example, KDS-4103, includes an amine base. In some embodiments, the amine base is a tertiary amine base. In other embodiments, the amine base is selected from among triethylamine, diisopropylethylamine, 1,2,2,6,6-pentamethylpiperidine, and tributylamine. In some other embodiments, the amine base is triethylamine. In some other embodiments, the tertiary amine base is triethylamine.

In certain embodiments, the process for preparing the alkylcarbamic acid aryl ester of Formula (I) includes isolating the alkylcarbamic acid aryl ester of Formula (I) (step (b)). In some embodiments, isolating the compound KDS-4103 includes filtration.

In one embodiment, KDS-4103 is prepared by the process outlined in Scheme 1.

Scheme 1. Synthesis of alkylcarbamic acid aryl esters of Formula (I).

KDS-4103

Scheme 1 outlines the process for the preparation of KDS-4103 in high yield, high purity and without the need for column chromatography. The alkyl carbamic acid aryl ester is prepared by treating 3'-hydroxybiphenyl-3-carboxamide (4) with cyclohexyl isocyanate (5) in the presence of triethylamine in a suitable solvent, such as, acetonitrile or ethanol. The reaction is performed at room temperature providing the compound KDS-4103 in yields greater than 86%. Under these reaction conditions the alkylcarbamic acid aryl ester product KDS-4103 precipitates out of the reaction mixture during the course of the reaction. The alkylcarbamic acid aryl ester is isolated by filtration in high yield and high purity without the need for column chromatography. This process provides the product in a crystalline form without the need for column chromatography or recyrstallization, which has favorable properties, such as, for example, effective particle size and increased oral bioavailability. In one embodiment, alkyl carbamic acid aryl esters are prepared by treating 3'-hydroxybiphenyl-3-carboxamide (4), with cyclohexyl isocyanate (5) in the presence of triethylamine in acetonitrile as the solvent. In another embodiment, the alkyl carbamic acid aryl ester KDS-4103 is are prepared by treating 3'-hydroxybiphenyl-3-carboxamide (4), with cyclohexyl isocyanate (5) in the presence of triethylamine in ethanol as the solvent. In one embodiment, the alkylcarbamic acid aryl ester of Formula (I) KDS-4103 is crystallized from acetonitrile or ethanol.

The process disclosed herein for the preparation of the alkylcarbamic acid aryl ester KDS-4103 contrasts to processes typically utilized for the preparation of alkylcarbamic acid aryl esters, such as for example, KDS-4103 (see Mor et al. and Piomelli et al.). Mor et al. and Piomelli et al, disclose a process for the preparation of the alkylcarbamic acid aryl ester of Formula (I), wherein 3'-hydroxybiphenyl-3-carboxamide (4) is treated with cyclohexyl isocyanate (5) in the presence of triethylamine in refluxing toluene. Using the process disclosed by Mor et al. and Piomelli et al. low yields of the alkylcarbamic acid aryl ester product is obtained. KDS-4103 is prepared in approximately 30% yield, and column chromatography is required in the purification step. The process disclosed herein for the preparation of the alkylcarbamic acid aryl ester of Formula (I), KDS-4103, satisfies the need for an efficient, cost effective, scaleable, and safe process for the preparation of this therapeutic compound on an industrial scale and laboratory scale.

In some embodiments, the process of preparing the alkylcarbamic acid aryl ester of Formula (I) includes preparing 3'-hydroxybiphenyl-3-carboxamide by a process that includes: treating 3-hydroxyphenyl boronic acid with a 3-bromobenzamide in the presence of a heterogeneous palladium catalyst, an inorganic base, a phase-transfer catalyst, and a suitable organic solvent.

In certain embodiments, the heterogeneous palladium catalyst is selected from among $PdCl_2$, $Pd(OAc)_2$, and $Pd(OH)_2$. In other embodiments, the heterogeneous palladium catalyst is $PdCl_2$. In certain embodiments, the inorganic base is selected from among $Li_2CO_3$, $Na_2CO_3$, $K_2CO_3$, $Cs_2CO_3$, and NaOH. In some embodiments, the inorganic base is $K_2CO_3$. In some embodiments, the phase transfer catalyst is a tetra-alkyl ammonium halide. In some other embodiments, the phase transfer catalyst is $nBu_4NBr$.

In some embodiments, the process for preparing 3'-hydroxybiphenyl-3-carboxamide includes a suitable organic solvent selected from among methanol, ethanol, benzene, toluene, 1,4-dioxane, tetrahydrofuran, and water. In some other embodiments, the process for preparing 3'-hydroxybiphenyl-3-carboxamide includes ethanol.

In one embodiment, 3'-hydroxybiphenyl-3-carboxamide can be prepared by the process outlined in Scheme 2.

Scheme 2. Synthesis of 3-phenylphenols.

2

+

3'-hydroxybiphenyl-3-carboxamide is prepared by utilizing a transition metal cross coupling reaction. Coupling of a phenyl boronic acid, such as 3-hydroxyphenylboronic acid (3), with a halo-phenyl, such as 3-bromobenzamide (2), in the presence of a heterogeneous transition metal catalyst, such as, for example, a heterogeneous palladium catalyst, provides compound (4), in yields greater than 86%.

Mor et al. and Piomelli et al. (see above) disclose the preparation of 3'-hydroxybiphenyl-3-carboxamide by a process that utilizes a phenyl boronic acid, a halo-phenyl, a homogeneous palladium catalyst (tetrakistriphenylphosphine palladium), and an aqueous base ($Na_2CO_3$), in a mixed solvent system (toluene/ethanol) under an oxygen-free atmosphere. Prolonged reaction times and high reaction temperatures are required in order to obtain the desired 3-phenylphenol product. The process disclosed by Mor et al. and Piomelli et al. uses 3-methoxyphenylboronic acid in the cross coupling reaction, which adds additional steps of deprotecting the methoxy moiety and purifying the 3-phenylphenol product. This reduces the overall efficiency of the process. The use of homogeneous palladium catalysts leads to carry-over of the heavy metal catalyst, which is not acceptable for the preparation of active pharmaceutical ingredients (API). In addition, dissociation of the triphenyl phosphine ligands, which is a common occurrence with homogeneous palladium-phosphine catalysts, leads to the formation of phosphine oxides and thus difficulties in the isolation of the desired 3-phenylphenol products, thereby necessitating column chromatography. Also, the homogeneous palladium catalyst suffers from poor air stability, which necessitates the use of stringent, oxygen-free reaction conditions.

Provided herein is a process for the preparation of 3'-hydroxybiphenyl-3-carboxamide that does not require heating, avoids homogeneous palladium catalysts, avoids phosphine containing catalysts, does not require oxygen-free reaction conditions, provides high yields of the desired 3-phenyl phenol and avoids column chromatography. Treatment of 3-bromobenzamide (2) with 3-hydroxyphenylboronic acid (3) in the presence of a heterogeneous, phosphine-free palladium catalysts, such as, palladium dichloride; a phase transfer catalyst, such as a tetraalkylammonium halide, such as tetrabutylammonium bromide; an inorganic base, such as potassium carbonate; in ethanol, provides the product in high yields, greater than 86%.

The process disclosed herein is suitable for large scale chemical production. The use of a heterogeneous phosphine-free palladium catalyst allows reactions to occur at room temperature in organic solvents, such as acetonitrile or etha- nol, avoids the need for oxygen-free systems, and significantly improves the process. Due to the heterogeneous nature of the palladium catalyst, contamination of the 3-phenylphenol product by transition metal species is dramatically reduced or eliminated altogether. Upon completion of the reaction, the reaction mixture is filtered and the solvent is removed, providing the desired product in high purity without a need for column chromatography.

In a certain embodiment 3-bromobenzamide is prepared by the process outlined in Scheme 3.

3-Bromobenzamide (2) is prepared by the partial hydrolysis of 3-bromobenzonitrile (1), with $NaBO_3$—$4H_2O$ in 80% yield. Alternatively, 3-bromobenzamide (2) can be prepared in 90% yield by treating 3-bromobenzonitrile (1) with hydrogen peroxide (30% solution in water) in the presence of sodium hydroxide, and methanol as the solvent. This reaction is scaleable and the product is obtained in high purity and yield, obviating the need for column chromatography.

In one embodiment, provided herein is a crystalline form of the compound KDS-4103

KDS-4103 which is characterized by a solid state X-ray powder diffraction XRPD pattern as shown in FIG. 1. In another embodiment, provided herein is a crystalline form of the compound KDS-4103, which is characterized by a solid state X-ray powder diffraction XRPD pattern as shown in FIG. 2.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

Provided herein are pharmaceutical compositions that include KDS-4103 and a pharmaceutically acceptable diluent(s), excipient(s), or carrier(s).

A pharmaceutical composition, as used herein, refers to a mixture of KDS-4103 with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical compositions will include at least KDS-4103 as an active ingredient in free-acid or free-base form, or in a pharmaceutically acceptable salt form.

The term "acceptable" with respect to a formulation, composition or ingredient, as used herein, means having no persistent detrimental effect on the general health of the subject being treated.

By "pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

"Bioavailability" refers to the percentage of the weight of compounds disclosed herein, such as, KDS-4103, dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which compounds disclosed herein, such as, KDS-4103, are absorbed into the general circulation when the pharmaceutical composition is taken orally as compared to intravenous injection.

"Blood plasma concentration" refers to the concentration of compounds disclosed herein, such as, KDS-4103, in the plasma component of blood of a subject. It is understood that the plasma concentration of KDS-4103 may vary significantly between subjects, due to variability with respect to metabolism and/or possible interactions with other therapeutic agents. In accordance with one aspect of the present invention, the blood plasma concentration of KDS-4103 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of KDS-4103 may vary from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

"Effective particle size," as used herein refers to and is determined on the basis of the volume weight average particle size as measured by conventional particle size measuring techniques well known to those skilled in the art. Such techniques include, for example, sedimentation field flow fractionation, photon correlation spectroscopy, light scattering, laser diffraction and disc centrifugation. For the purposes of the compositions, formulations and methods described herein, effective particle size is the volume mass average particle size as determined using light scattering methods, e.g. Horiba LA-950. For example, an effective particle size of 5.9 μm means that 50% of the particles by weight are less than 5.9 μm and 50% of the particles by weight are greater than 5.9 μm.

The formulations that include KDS-4103 described herein include KDS-4103 particles existing in crystalline form with KDS-4103 particles having an average effective particle size less than about 17.0 μm, an effective average particle size less than about 15.0 μm, an effective average particle size less than about 13.0 μm, an effective average particle size less than about 11.0 μm, an effective average particle size less than about 7.0 μm, an effective average particle size less than about 6.0 μm, an effective average particle size less than about 5.0 μm, or an effective average particle size less than about 4.0 μm By "an effective average particle size of less than about 6.0 μm" it is meant that at least 50% of the KDS-4103 particles by weight have a particle size of less than about 6.0 μm when measured by techniques described above or known in the art. In other embodiments, at least about 70%, at least 80%, or at least about 90%, or at least about 95% of the KDS-4103 particles by weight have a particle size of less than the effective average, i.e., less than about 6.0 μm, less than about 5.0 μm less than about 4.0 μm, less than about 3.0 μm, or less than about 2.0 μm. In one embodiment, the particles of KDS-4103 have a particle size distribution wherein 90% of the particles by weight have an effective particle size by weight between about 2.2 μm and about 12.2 μm. In another embodiment, the particles of KDS-4103 have a particle size distribution wherein 80% of the particles by weight have an effective particle size by weight between about 2.2 μm and about 12.2 μm.

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include KDS-4103, can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In various embodiments, the particles of KDS-4103, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

Compositions provided herein include the compound of Formula (I) KDS-4103. In certain embodiments, compositions provided herein include particles of KDS-4103, with a XRPD pattern as shown in FIG. 1, and a particle size distribution ranging from about 1.1 μm to about 89.3 μm, with an effective average particle size of about 13.9 μm. In some embodiments, about 80% of the particles in the compositions provided herein include particles of KDS-4103, with a XRPD pattern as shown in FIG. 1, and a particle size distribution ranging from about 5.0 μm to about 35.5 μm, with an effective average particle size of about 13.9 μm. In other embodiments, about 60% of the particles in the compositions provided herein include particles of KDS-4103, with a XRPD pattern as shown in FIG. 1, and a particle size distribution ranging from about 7.0 μm to about 28.2 μm, with an effective average particle size of about 13.9 μm. In other embodiments, about 40% of the particles in the compositions provided herein include particles of KDS-4103, with a XRPD pattern as shown in FIG. 1, and a particle size distribution ranging from about 10.0 μm to about 22.4 μm, with an effective average particle size of about 13.9 μm. In other embodiments, about 20% of the particles in the compositions provided herein include particles of KDS-4103, with a XRPD pattern as shown in FIG. 1, and a particle size distribution ranging from about 11.2 μm to about 17.8 μm, with an effective average particle size of about 13.9 μm. In other embodiments, about 10% of the particles in the compositions provided herein include particles of KDS-4103, with a XRPD pattern as shown in FIG. 1, and a particle size distribution ranging from about 12.6 μm to about 15.8 μm, with an effective average particle size of about 13.9 μm In certain embodiments, compositions provided herein include particles of KDS-4103, with a XRPD pattern as shown in FIG. 2, and a particle size distribution ranging from about 0.5 μm to about 31.6 μm, with an effective average particle size of about 5.9 μm. In some embodiments, about 80% of the particles in the compositions provided herein include particles of KDS-4103, with a XRPD pattern as shown in FIG. 2, and a particle size distribution ranging from about 2.5 μm to about 12.8 μm, with an effective average particle size of about 5.9 μm. In other embodiments, about 60% of the particles in the compositions provided herein include particles of KDS-4103, with a XRPD pattern as shown in FIG. 2, and a particle size distribution ranging from about 3.5 μm to about 10.0 μm, with an effective average particle size of about 5.9 μm. In some other embodiments, about 40% of the particles in the compositions provided herein include particles of KDS-4103, with a XRPD pattern as shown in FIG. 2, and a particle size distribution ranging from about 4.4 μm to about 8.9 μm, with an effective average particle size of about 5.9 μm. In some embodiments, about 20% of the particles in the compositions provided herein include particles of KDS-4103, with a XRPD pattern as shown in FIG. 2, and a particle size distribution ranging from about 5.0 μm to about 7.0 μm, with an effective average particle size of about 5.9 μm. In some embodiments, about 10% of the particles in the compositions provided herein include particles of KDS-4103, with a XRPD pattern as shown in FIG. 2, and a particle size distribution ranging from about 5.6 μm to about 6.3 μm, with an effective average particle size of about 5.9 μm.

In certain embodiments, compositions provided herein include particles of KDS-4103 with an effective average particle size less than about 10.0 μm, less than about 9.0 μm, less than about 8.0 μm, less than about 7.0 μm, less than about 6.0 μm, less than about 5.0 μm, less than about 4.0 μm, or less than about 3.0 μm.

EXAMPLES

The person skilled in the art may further appreciate various aspects and advantages of the present disclosure upon review of the following illustrative and non-limiting examples:

Example 1

Synthesis of 3-Bromobenzamide using Sodium Perborate

To a 2-liter round bottom flask was added 3-bromobenzonitrile (138 g, 0.76 mol, 1 equivalent) followed by 1,4-dioxane (830 mL), water (830 mL) and sodium perborate tetrahydrate (322 g, 2.1 mol., 2.75 equivalents). The reaction mixture was heated to 80° C. for 16 hours. The clear solution was cooled to room temperature, and diluted with water (4 L). The desired product precipitated during the addition of water, and was filtered and dried under high vacuum to yield the product as a white solid (1117.52 g, 0.59 mol.). The filtrate was cooled to 0° C. and stored overnight at 0° C. A second crop of product was collected by filtration (12.2 g., 0.06 mol). 3-Bromobenzamide was obtained as a white crystalline solid (129.7 g 0.65 mol., 86%).

Example 2

Synthesis of 3-Bromobenzamide Using Hydrogen Peroxide

To a 5 L 3-neck round bottom flask was added water (900 mL) followed by NaOH (66 g, 1.65 mol, 1 equivalent) and MeOH (900 mL). The reaction mixture was cooled to approximately 0-10° C. and 3-bromobenzonitrile (300 g, 1.65 mol) was added. The reaction mixture was stirred vigorously and $H_2O_2$ (30% in water, 500 mL, 82.45 mol, 2.4 equivalents) was added. The rate of addition was adjusted to maintain a reaction temperature below 25° C. Upon completion of the addition of the hydrogen peroxide, the reaction mixture was stirred for 2 hours at 10° C. The reaction mixture was then warmed to room temperature and stirred for an additional 16-18 hours. The reaction mixture was filtered and the filtercake was washed with water (3×500 mL). The product was dried under vacuum at 40-45° C. to obtain a white solid (302.04 g, 0.151 mol, 92%).

Example 3

Synthesis of 3'-Hydroxybiphenyl-3-Carboxamide on a Laboratory Scale

To a 5 L 3-neck round bottom flask was charged with 3-bromobenzamide (128.29 g, 0.64 mol), EtOH (1274 mL), $PdCl_2$ (0.588 g, 3.3 mmol, 0.005 equivalents), 3-hydroxyphenyl boronic acid (93 g, 0.67 mol. 1.05 equivalents), $K_2CO_3$ (177 g, 1.28 mol, 2 equivalents) and $nBu_4NBr$ (10.3 g, 0.032 mol, 0.05 equivalents). The reaction mixture was stirred at room temperature for approximately 16 hours. Upon completion of the reaction, a 10% aqueous HCl solution was added to the reaction mixture until the pH reached 1-2. The reaction mixture was extracted with EtOAc. The organic phases were combined and filtered through celite. The organic solvents were then removed under vacuum to obtain an orange solid. The solid was dissolved in acetone (200-300 mL) and water (1700 mL) was added. The reaction mixture was stirred for 1 hour at approximately 5-10° C. The product was collected by filtration as a white solid and dried under vacuum at 40-45° C. (132.9 g, 0.62 mol, 98%).

Example 4

Synthesis of 3'-Hydroxybiphenyl-3-Carboxamide on an Industrial Scale

A 50 L reactor was charged with 3-hydroxyphenylboronic acid (1.776 kg, 12.88 mol, 1.05 eq), 3-bromobenzamide (2.453 kg, 12.26 mol, 1.0 eq), tetrabutylammonium bromide (0.198 kg, 0.61 mol, 0.05 eq), $PdCl_2$ (0.011 kg, 0.061 mol, 0.005 eq), and EtOH (9.689 kg). To the reaction mixture at 20-25° C., with moderate stirring, was added a slurry of $K_2CO_3$ (3.390 kg, 24.53 mol, 2 eq) in EtOH (4.84 kg). The $K_2CO_3$ container was rinsed with EtOH (4.84 kg) into the reactor. The reaction mixture was stirred at 20-25° C. for approximately 3-5 hours and monitored by thin layer chromatography (TLC) (hexanes:EtOAc 6:4). After the reaction was judged to be complete, 10% aq. HCl was added to the reaction mixture until the pH reached 1-2. Additional 10% aq. HCl was added, resulting in a final pH less than 1. The solution was agitated for approximately 35 minutes at 20-25° C. Approximately 12 liters of the solution was drained off and set aside. The remaining reaction mixture was diluted with EtOAc and washed with water (0.17 mL of EtOAc was added per mL of solution, and 0.294 mL of water per mL of solution). The organic phases were combined and concentrated in vacuo. Once the organic phases were reduced in volume to about 9 L, the mixture was transfered to reactor and 32 L of water was added. The temperature of the mixture was adjusted to 0-5° C., and it was agitated for 30 minutes. The product precipitated from the mixture and was filtered. The filter cake was washed with water from the reactor and dried at ambient temperature for about 18 hours, yielding 2.212 Kg (85%) of a white solid.

Example 5

Synthesis of KDS-4103 in Ethanol on a Laboratory Scale

To a stirred suspension of 3'-hydroxybiphenyl-3-carboxamide (132.9 g, 0.62 mol) in ethanol (1329 mL) was added triethylamine (TEA) (95.6 mL, 0.69 mol, 1.1 equivalents) and cyclohexyl isocyanate (79.7 ml, 0.62 mol, 1.0 equivalent). The reaction mixture was stirred at room temperature for 16 hours. An additional amount of cyclohexyl isocyanate (23.9 mL, 0.18 mol., 0.2 equivalents) was added to the reaction mixture. The reaction mixture was stirred for an additional 16 hours. The product was isolated by cooling the reaction mixture with an ice bath and filtering. The filtercake was washed with cold EtOH (300 mL). A white chrystalline solid was obtained after drying at 25-30° C. (187.7 g, 0.55 mol., 89%). The crystalline product was characterized by X-ray powder diffraction and the X-ray powder diffraction XRPD pattern is shown in FIG. 1.

Example 6

Synthesis of KDS-4103 in Acetonitrile on a Laboratory Scale

Reaction conditions were used as stated for Example 5, except that acetonitrile was used as organic solvent instead of EtOH. The product was obtained in 80-89% yield. The crystalline product was characterized by X-ray powder diffraction and the X-ray powder diffraction XRPD pattern is shown in FIG. 2.

Example 7

Synthesis of KDS-4103 in Ethanol on an Industrial Scale

A 50 L reactor was charged with 3'-hydroxybiphenyl-3-carboxamide (2.202 kg, 10.33 mol, 1.0 eq), EtOH (17.45 kg), triethylamine (1.358 kg, 13.42 mol, 1.3 eq) and cyclohexyl isocyanate (1.68 kg, 13.42 mol, 1.3 eq). The reaction contents were allowed to stir under agitation at 20-25° C. for about 4 hours. The product was isolated by cooling the reaction mixture to 0-5° C. for about 1 hour and filtering. The filter cake was dried with nitrogen gas at ambient temperature for about 16 hours. The product was then triturated with EtOH (8.7 kg) at 0-5° C. for a minimum of 10 minutes and then filtered. The solid was washed with cold EtOH (5.265 kg). The product was dried at 30° C. for approximately 20 hours to obtain 2.996 kg of a white solid, (86%).

Example 8

Recrystallization of KDS-4103 from Ethanol

KDS-4103 was suspended in sufficient volume of ethanol and heated to dissolve. The solution was slowly cooled to room temperature and then cooled to 0-5° C. The white precipitate was filtered and was washed with cold EtOH. The product was dried at 30° C. for approximately 20 hours. The recrystallized KDS-4103 had the same XRPD pattern as depicted in FIG. 1.

Example 9

Recrystallization of KDS-4103 from Acetonitrile

KDS-4103 was suspended in sufficient volume of acetonitrile and heated to dissolve. The solution was slowly cooled to room temperature and then cooled to 0-5° C. The white precipitate was filtered and was washed with cold acetonitrile. The product was dried at 30° C. for approximately 20 hours. The recrystallized KDS-4103 had the same XRPD pattern as depicted in FIG. 2.

Example 10

X-Ray Powder Diffraction XRPD Pattern Determination of KDS-4103 from Ethanol A crystalline form of KDS-4103, prepared from the reaction of Example 5 or Example 7, or through recrystallization of KDS-4103 in ethanol was characterized by X-ray Powder Diffraction (XRPD) pattern, which are useful in characterizing the polymorph of KDS-4103 disclosed herein.

The sample was prepared by a normal front packing technique in a deep large Aluminum sample holder and run on a Siemens D5000 Diffractometer System operating st 50 kV/35 mA. A high powe, line focus Cu-Kα-source was used combined with a solid state Kevex detector. The experimental data were collected on step scan mode (ss: 0.02/t: 1.8s) within the range of 2.0°-35° (2-theta). The data obtained were processed using Diffrac Plus™ Software. XRPD data is shown in FIG. 1, and tabulated in Table 1.

TABLE 1

XRPD pattern peak data for KDS-4103 from EtOH.

| 2-Theta | D spacing (angstroms) | I/Imax (%) |
|---|---|---|
| 2.86 | 30.844 | 55.9 |
| 5.74 | 15.384 | 100 |
| 8.64 | 10.221 | 44.4 |
| 14.41 | 6.141 | 3.6 |
| 15.29 | 5.791 | 4.9 |
| 16.64 | 5.322 | 4.8 |
| 16.93 | 5.232 | 10.6 |
| 17.22 | 5.145 | 16.3 |
| 17.42 | 5.087 | 14.7 |
| 18.53 | 4.783 | 4 |
| 20.2 | 4.392 | 38 |
| 20.32 | 4.366 | 42.2 |
| 20.76 | 4.276 | 4.6 |
| 21.48 | 4.134 | 7.9 |
| 22.52 | 3.945 | 18.6 |
| 23.13 | 3.843 | 9.7 |
| 23.44 | 3.792 | 6.1 |
| 24.64 | 3.61 | 1.7 |
| 25.86 | 3.442 | 1.9 |
| 26.31 | 3.385 | 1.2 |
| 26.94 | 3.307 | 1.8 |
| 27.36 | 3.257 | 2.1 |
| 28.59 | 3.119 | 4 |
| 29.27 | 3.049 | 2.4 |
| 29.96 | 2.98 | 4.4 |
| 30.56 | 2.923 | 2.7 |
| 30.7 | 2.91 | 3.7 |
| 32.97 | 2.714 | 1.7 |
| 33.8 | 2.65 | 1.2 |
| 34.29 | 2.613 | 1.3 |

Example 11

X-Ray Powder Diffraction XRPD Pattern Determination of KDS-4103 from Acetonitrile A crystalline form of KDS-4103, prepared from the reaction of Example 6, or through recrystallization of KDS-4103 in acetonitrile was characterized by X-ray Powder Diffraction (XRPD) pattern, which are useful in characterizing the polymorph of KDS-4103 disclosed herein.

The sample was prepared by a normal front packing technique in a deep large Aluminum sample holder and run on a Siemens D5000 Diffractometer System operating st 50 kV/35 mA. A high powe, line focus Cu-Kα-source was used combined with a solid state Kevex detector. The experimental data were collected on step scan mode (ss: 0.02/t: 1.8s) within the range of 2.0°-35° (2-theta). The data obtained were processed by Diffrac Plus™ Software. XRPD data is shown in FIG. 2, and tabulated in Table 2.

TABLE 2

XRPD pattern peak data for KDS-4103 from acetonitrile.

| 2-Theta | D spacing (angstroms) | I/Imax (%) |
|---|---|---|
| 2.672 | 33.035 | 82.5 |
| 5.299 | 16.665 | 24.5 |
| 7.943 | 11.122 | 2.9 |
| 10.598 | 8.341 | 17.3 |
| 13.253 | 6.675 | 10.6 |
| 15.925 | 5.561 | 10.8 |
| 16.911 | 5.239 | 15.2 |
| 17.559 | 5.047 | 25.5 |
| 17.898 | 4.952 | 51.6 |
| 18.412 | 4.815 | 100 |
| 18.987 | 4.67 | 20.9 |
| 19.356 | 4.582 | 49.3 |
| 20.079 | 4.419 | 87.9 |
| 20.537 | 4.321 | 22.5 |
| 21.1 | 4.207 | 23.5 |
| 21.375 | 4.153 | 35.5 |
| 22.374 | 3.97 | 29.6 |
| 23.147 | 3.839 | 21.9 |
| 23.905 | 3.719 | 5.3 |
| 24.623 | 3.613 | 7.5 |
| 25.039 | 3.553 | 27 |
| 25.784 | 3.452 | 19.9 |
| 26.756 | 3.329 | 40.9 |
| 27.974 | 3.187 | 7.6 |
| 29.157 | 3.06 | 6.8 |
| 30.712 | 2.909 | 4.2 |
| 31.871 | 2.806 | 7.1 |
| 33.076 | 2.706 | 3.3 |
| 33.935 | 2.639 | 8.8 |
| 34.695 | 2.583 | 3.5 |

Example 12

Particle Size Determination of KDS-4103 Polymorph from EtOH

Figure 3:
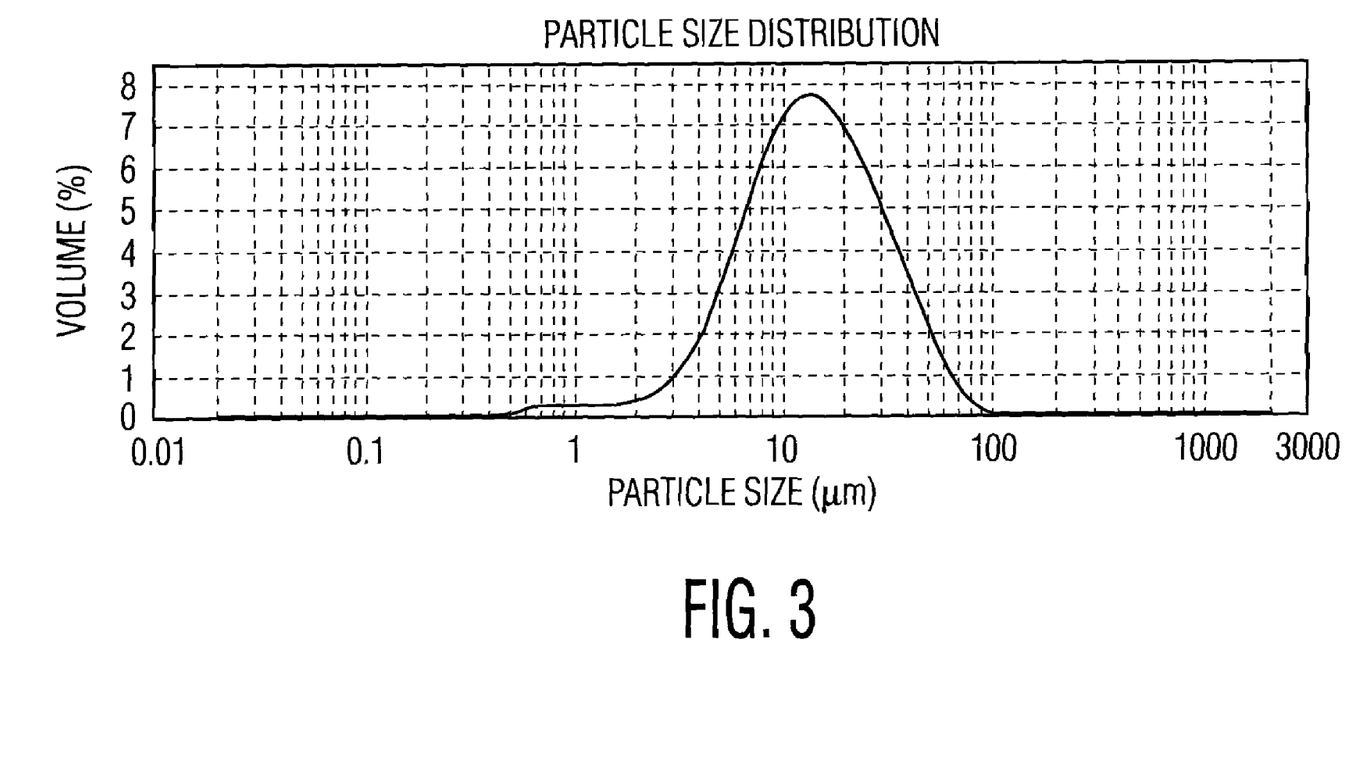
FIG. 3 is the particle size distribution of the crystalline form of KDS-4103 crystallized from ethanol.

Particle size determination of the polymorphs of KDS-4103 was carried out using a Malvern Mastersizer 2000 Hydro S system. KDS-4103 was dispersed in hexane, 1 minute sonication (47 kHz), 10,000 sweeps. KDS-4103 crystallized from ethanol had a particle distribution as shown in FIG. 3. Crystalline particles of KDS-4103 from ethanol had a particle distribution ranging from about 1.1 μm to about 89.3 μm, with an average effective average particle size of about 13.9 μm.

Example 13

Particle Size Determination of KDS-4103 Polymorph from Acetonitrile

Figure 4:
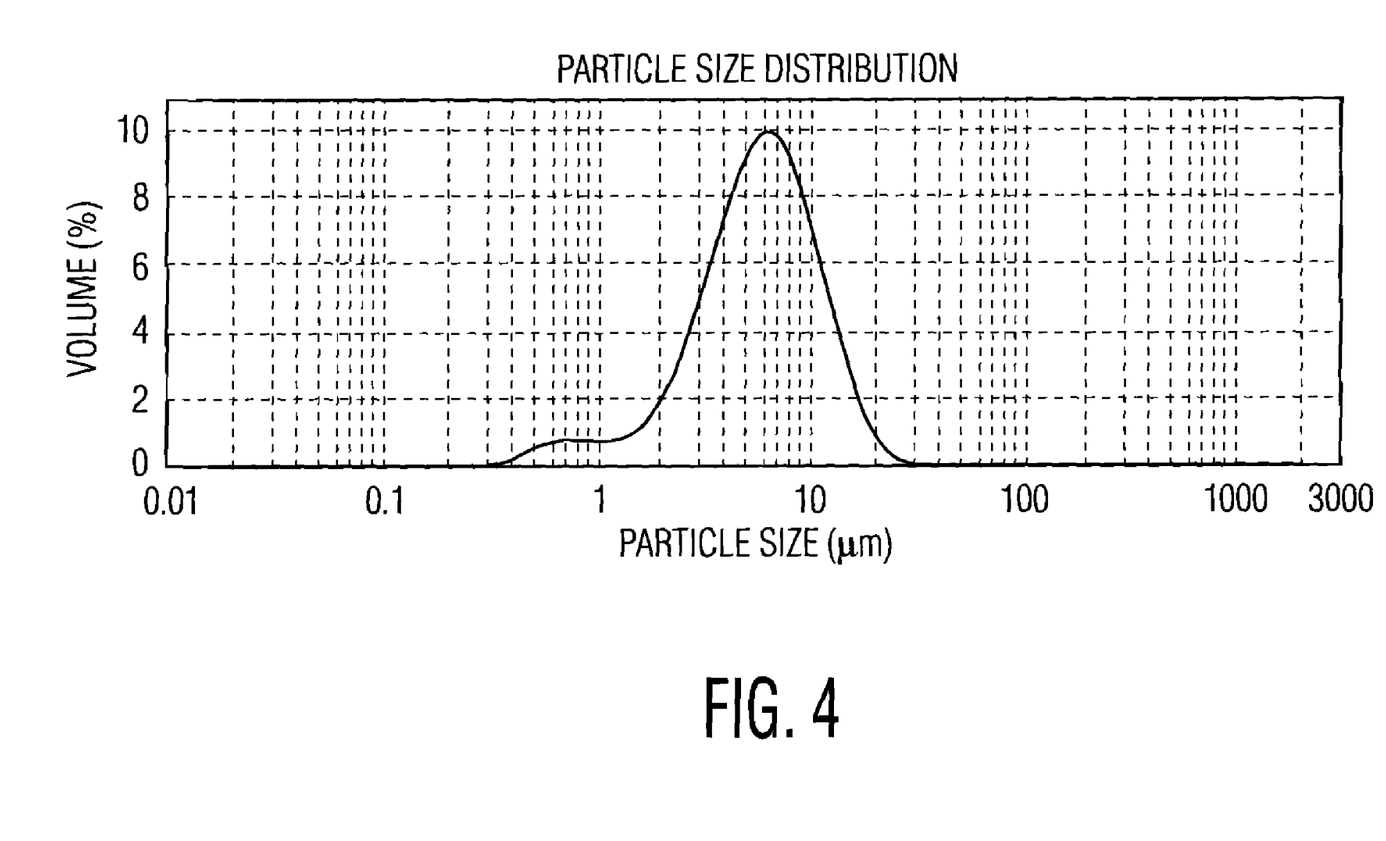
FIG. 4 is the particle size distribution of the crystalline form of KDS-4103 crystallized from acetonitrile.

Particle size determination of the polymorphs of KDS-4103 was carried out using a Malvern Mastersizer 2000 Hydro S system. KDS-4103 was dispersed in hexane, 1 minute sonication (47 kHz), 10,000 sweeps. KDS-4103 crystallized from acetonitrile had a particle distribution as shown in FIG. 4. Crystalline particles of KDS-4103 from acetonitrile had a particle distribution ranging from about 0.5 μm to about 31.6 μm, with an average effective average particle size of about 5.9 μm.

Example 14

Oral Bioavailability Determination of KDS-4103 Polymorphs

Figure 5:
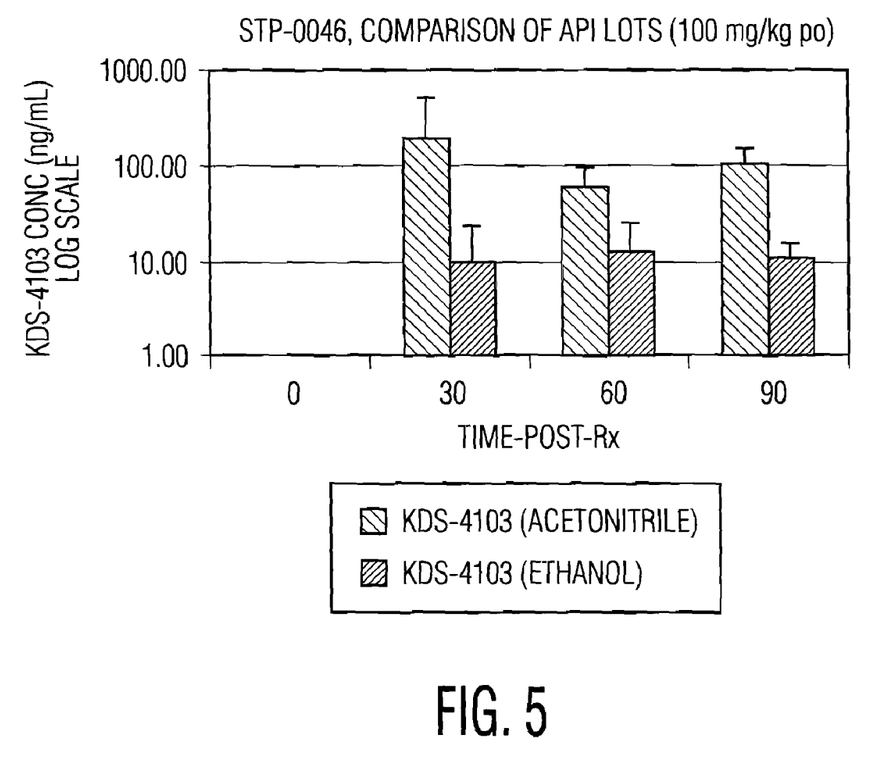
FIG. 5 is a comparison of the oral bioavailability in rats of the two polymorphs of KDS-4103, crystallized from ethanol and acetonitrile.

The pharmacokinetic properties of KDS-4103 were assessed in rats following oral administration as a suspension. To test the oral bioavailability of the KDS-4103 polymorphs from acetonitrile and ethanol (see Examples above), suspensions of the KDS-4103 polymorphs were prepared for oral administration. The two polymorphs of KDS-4103, from acetonitrile and ethanol, were prepared as separate 100 mg/mL suspensions in 0.5% sodium carboxymethyl cellulose, 0.5% simethicone, and 0.4% Polysorbate 80 in water (w/v). The suspensions of KDS-4103 were administered to two separate groups of rats at a dose of 1 ml/kg of KDS-4103 via oral gavage. Animals were sacrificed at 30, 60 and 90 minutes post-dose in each group. Collection of $K_3EDTA$ was acheived via cardiac puncture. Samples were analyzed for KDS-4103 concentrations. The results are presented in FIG. 5. and Table 3. Rats that were treated with the polymorph of KDS-4103 obtained from acetonitrile had increased levels of the compound in circulation compared to rats that were treated with the polymorph of KDS-4103 obtained from EtOH. The suspensions containing the polymorph of KDS-4103 from acetonitrile, having the smaller effective average particle size distribution, had increased bioavailability.

TABLE 3

Plasma concentrations of KDS-4103 polymorphs after oral administration to rats.

| Time (minutes) | KDS-4103 polymorph from acetonitrile, [KDS-4103] (ng/mL) | KDS-4103 polymorph from ethanol, [KDS-4103] (ng/mL) |
|---|---|---|
| 0 | 0.00 | 0.00 |
| 30 | 196.06 | 9.62 |
| 60 | 58.95 | 12.60 |
| 90 | 105.36 | 10.74 |

Example 15

Pharmaceutical Compositions

Example 15a

Parenteral Composition

To prepare a parenteral pharmaceutical composition suitable for administration by injection, 100 mg of a compound described herein is dissolved in DMSO and then mixed with 10 mL of 0.9% sterile saline. The mixture is incorporated into a dosage unit form suitable for administration by injection.

Example 15b

Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example 15c

Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 15d

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 15e

Rectal Gel Composition

To prepare a pharmaceutical composition for rectal delivery, 100 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 15f

Topical Gel Composition

To prepare a pharmaceutical topical gel composition, 100 mg of a compound described herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 15g

Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested to persons skilled in the art are to be included within the spirit and purview of this application and scope of the appended claims. All publications, patents, and patent applications cited herein are hereby incorporated by reference for all purposes.

The invention claimed is:

1. A process for preparing of the alkylcarbamic acid aryl ester of Formula (I):

comprising the steps of:
(a) reacting cyclohexyl isocyanate with 3'-hydroxybiphenyl-3-carboxamide in the presence of an amine base in a suitable non-aromatic solvent; and
(b) isolating the alkylcarbamic acid aryl ester KDS-4103.

2. The process of claim 1, wherein the suitable non-aromatic solvent is acetonitrile or ethanol.

3. The process of claim 1, wherein the suitable non-aromatic solvent is acetonitrile.

4. The process of claim 1, wherein the amine base is a tertiary amine base.

5. The process of claim 4, wherein the tertiary amine base is selected from among triethylamine, diisopropylethylamine, 1,2,2,6,6-pentamethylpiperidine, and tributylamine.

6. The process of claim 5, wherein the amine base is triethylamine.

7. The process of claim 1, wherein the 3'-hydroxybiphenyl-3-carboxamide is prepared by a process comprising treating 3-hydroxyphenyl boronic acid with 3-bromobenzamide in the presence of a heterogeneous palladium catalyst, an inorganic base, a phase-transfer catalyst, and a suitable organic solvent.

8. The process of claim 7, wherein the heterogenous palladium catalyst is selected from among $PdCl_2$, $Pd(OAc)_2$, and $Pd(OH)_2$.

9. The process of claim 8, wherein the heterogeneous catalyst is $PdCl_2$.

10. The process of claim 8, wherein the inorganic base is selected from among $Li_2CO_3$, $Na_2CO_3$, $K_2CO_3$, $Cs_2CO_3$, and NaOH.

11. The process of claim 10, wherein the inorganic base is $K_2CO_3$.

12. The process of claim 8, wherein the phase transfer catalyst is a tetra-alkyl ammonium halide.

13. The process of claim 12, wherein the phase transfer catalyst is $nBu_4NBr$.

14. The process of claim 8, wherein the suitable organic solvent is selected from among methanol, ethanol, benzene, toluene, 1,4-dioxane, tetrahydrofuran, and water.

15. The process of claim 14, wherein the suitable organic solvent is ethanol.

16. A crystalline form of the compound KDS-4103

KDS-4103 having D-spacings determined by x-ray powder diffraction, Cu-K alpha of

| 2-Theta | D spacing (angstroms) |
|---|---|
| 2.672 | 33.035 |
| 5.299 | 16.665 |
| 7.943 | 11.122 |
| 10.598 | 8.341 |
| 13.253 | 6.675 |
| 15.925 | 5.561 |
| 16.911 | 5.239 |
| 17.559 | 5.047 |

-continued

| 2-Theta | D spacing (angstroms) |
|---|---|
| 17.898 | 4.952 |
| 18.412 | 4.815 |
| 18.987 | 4.67 |
| 19.356 | 4.582 |
| 20.079 | 4.419 |
| 20.537 | 4.321 |
| 21.1 | 4.207 |
| 21.375 | 4.153 |
| 22.374 | 3.97 |
| 23.147 | 3.839 |
| 23.905 | 3.719 |
| 24.623 | 3.613 |
| 25.039 | 3.553 |
| 25.784 | 3.452 |
| 26.756 | 3.329 |
| 27.974 | 3.187 |
| 29.157 | 3.06 |
| 30.712 | 2.909 |
| 31.871 | 2.806 |
| 33.076 | 2.706 |
| 33.935 | 2.639 |
| 34.695 | 2.583. |

17. A pharmaceutical composition comprising the compound KDS-4103 of claim 16 formulated for oral administration.

* * * * *